United States Patent [19]

Batchelder et al.

[11] Patent Number: 5,158,690
[45] Date of Patent: Oct. 27, 1992

[54] THERMOPHORETIC FILTERING OF LIQUIDS

[75] Inventors: John S. Batchelder, Somers; Douglas W. Cooper, Millwood; Donald M. DeCain, New York; Walter W. Hildenbrand, Brewster, all of N.Y.

[73] Assignee: International Business Machines Corporation, Armonk, N.Y.

[21] Appl. No.: 837,507

[22] Filed: Feb. 18, 1992

[51] Int. Cl.⁵ ............................................. B01D 35/18
[52] U.S. Cl. ..................................... 210/775; 210/176
[58] Field of Search ................. 210/176, 742, 774, 775

[56] References Cited

U.S. PATENT DOCUMENTS

| | | | |
|---|---|---|---|
| 2,258,594 | 10/1941 | Brewer et al. | 183/115 |
| 2,521,112 | 9/1950 | Beams | 210/52.5 |
| 2,540,977 | 2/1951 | Arnold | 260/666 |
| 2,541,071 | 2/1951 | Jones et al. | 260/97.7 |
| 4,048,063 | 9/1977 | Cheng | 210/775 |
| 4,153,546 | 5/1979 | Hammel et al. | 210/41 |
| 4,430,271 | 2/1984 | Barton et al. | 260/458 R |
| 4,643,833 | 2/1987 | Aulich et al. | 210/714 |

OTHER PUBLICATIONS

G. S. McNab et al., "Thermophoresis in Liquids", Journal of Colloid and Interface Science, vol. 44, No. 2, Aug. 1973, pp. 339-346.

A. F. Andreev, "Thermophoresis in Liquids", Sov. Phys. JETP, vol. 67, No. 1, Jan. 1988, pp. 117-120.

*Primary Examiner*—Frank Spear
*Attorney, Agent, or Firm*—Philip J. Feig

[57] ABSTRACT

A thermophoretic filter cell for the filtering of particles from a liquid is constructed in a particular manner so that the liquid introduced into the filter acts as the heat sink. The cell is designed so that the thermophoretic velocity of the particles in the liquid equals or exceeds the velocity (flow rate per unit area) at which the liquid is passing through the filter.

8 Claims, 1 Drawing Sheet

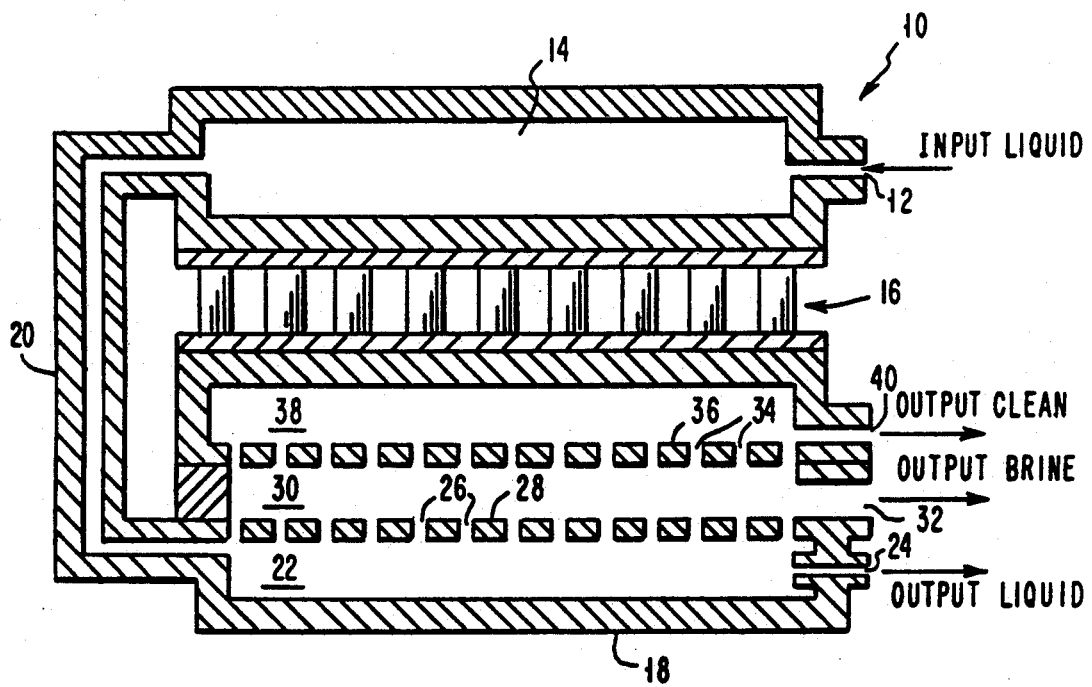

THERMOPHORETIC FILTERING OF LIQUIDS

BACKGROUND OF THE INVENTION

The present invention relates to the filtering of particles from a liquid and particularly to the filtering of sub-micron particles from liquids using a thermophoretic filter.

Liquids are much more difficult to filter than gases for several physical reason. Brownian motion causes aerosol particles to travel much farther in gases than in liquids, providing an opportunity for the particles to collide with and stick to a membrane. Also, viscous drag is much smaller in gasses (for the same volume of material) so that smaller pore sized filters can be used in gasses without extraordinary pressure drops. Adhesion of particles to surfaces in liquids is generally less than in gasses, so that particles captured on surfaces in liquids are more likely to be re-entrained. Most filters for liquids rely on sieving, using pores having dimensions smaller than the particles to be captures; this leads to more clogging problems than occur with filter for gasses. Moreover, water hammer effects can destroy liquid filters. In addition, poor initial wetting of filter membranes can reduce the performance of liquid filters. There is no porous membrane material that has demonstrated good filter performance in all of the semiconductor process liquids currently in use.

Given all these problems, techniques have been developed, other than sieving, which provide partial solutions.

In electrophoretic techniques dipole fields are used in molecular separations. Multipole fields are useful for filtering liquids having sufficiently low electrical conductivity. Uniform electric fields can be used to remove charged particles from high-resistivity liquids. A general difficulty with using electric fields is that although most particles in solutions are charged, the magnitude and sign of the charge depends upon the pH of the solution, the type of material to be filtered and the type of solution. Moreover, any un-charged particles will not be filtered. These limitations restrict the applicability of filtering using electrophoresis techniques.

Dielectrophoretic techniques rely upon inhomogeneous electric fields causing material (or solution) of higher dielectric constant to displace those of lower dielectric constant. The technique will filter uncharged particles, but the liquids must have a low electrical conductivity thereby restricting the applicability of the technique in certain filtering application.

Magnetophoretic techniques apply inhomogeneous magnetic fields to exert differing forces on materials suspended in liquids depending upon the magnetic susceptibility. While the technique provides a very important effect in separation of materials in the field of waste re-cycling, it appears too inefficient for application in ultra-small particle separation.

One way to increase the liquid volume that a particle counter or other inspection instrument inspects is to pre-concentrate the particles into a smaller volume of liquid. If a fluid has a thermal gradient, there is a differential pressure applied to the particles causing them to migrate from the heat source. Such an effect is referred to as thermophoresis. The present invention relies upon the thermophoresis effect in the filter forming the present invention.

Thermophoresis has been observed in gasses for a long period of time. See, for instance, the bock by W. C. Hinds entitled "Aerosol Technology" published by Wiley Interscience in 1982. More recently, the thermophoresis effect has been observed in liquids and reported by G. S. McNab and A. Mesisen in an article entitled "Thermophoresis in Liquids", J. Colloid and Interface Science, V. 44, n. 2, 339 (1973). The article describes experiments where particles dispersed in a fluid trapped between two plates of differing temperatures will migrate towards and eventually deposit on the colder plate. Such an arrangement is not satisfactory for use as a liquid filter. Particle deposition on the surface of a flow cell or flow cavity is not a permanent effect. Vibration, turbulence and pressure fluctuations can re-release the particles back into the liquid flow stream.

U.S. Pat. No. 2,541,071 refers to a thermophoretic apparatus for the separation of two or more components of a mixture in a liquid by means of liquid thermal diffusion, where a mixture to be separated passes between a cold plate and a hot plate. In theory such an apparatus could be used to separate particles from a liquid. The problem encountered when using a cold plate as a heat sink is described hereinabove.

The thermophoretic force is inversely proportional to the thermal conductivity of the particle. The particle and the liquid can have equal thermal conductivity and a thermophoretic force will still be manifest. As a result, the particles can be sorted as a function of their thermal conductivity. Furthermore, the thermophoretic effect has very little sensitivity to particle size over a wide range of particle sizes, thereby enabling the technique to work with sub-microscopic particles.

SUMMARY OF THE INVENTION

The present invention provides a solution to the problems and limitations encountered in prior thermophoresis apparatus. Specifically, a thermophoresis filter cell is constructed in a particular manner so that the liquid introduced into the filter acts as the heat sink. As a result, particles will concentrate in the liquid rather than on a solid surface of the filter. This allows use of the filter cell as a particle concentrator.

Another discovery uncovered in connection with the present invention is that it is not necessary for the thermophoretic velocity of the particles to be equal to or greater than the velocity at which the liquid is being injected into the filter in order for the filter to operate properly. To the contrary, it s only necessary that the thermophoretic velocity of the particles within the filter exceeds the velocity (flow rate per unit area) at which the liquid is passing through the filter.

The present invention provides a filter apparatus which concentrates the particles from a large volume of liquid into a small volume of liquid, thereby facilitating the inspection of the liquid for small particles.

Also, in the filter itself there are no holes smaller than approximately 400 microns and the holes are actually slots, therefore the filter does not clog. The thermally conducting surfaces of the filter can be fabricated from materials such as sapphire, stainless steel, diamond, manganese oxide and cubic zirconium and the non-thermally conducting surfaces of the filter can be fabricated from inert materials such as Teflon so that the filter is compatible with almost any liquid. Moreover, the performance of the filter is generally independent of the liquid pressure, provided the liquid flow velocity meets the above criteria.

A principal object of the present invention is therefore, the provision of thermophoretic filter for liquids where a liquid injected into the filter acts as the heat sink for the filter.

Another object of the invention is the provision of a thermophoretic filter in which the thermophoretic velocity of the particles within the filter exceeds the velocity (flow rate per unit area) of the liquid passing through the filter.

A further object of the invention is the provision of a thermophoretic filter for concentrating particles in a liquid into a smaller volume of liquid.

Further and still other objects of the present invention will become more clearly apparent when the following description is read in conjunction with the accompanying drawing.

BRIEF DESCRIPTION OF THE DRAWING

The sole FIGURE is a cross-section view of a preferred embodiment of a thermophoretic filter.

DETAILED DESCRIPTION

Referring now to the sole FIGURE, there is shown a cross-sectional view of a preferred embodiment of a thermophoretic filter comprising the present invention.

Unfiltered liquid containing particles to be filtered flows into thermophoretic filter 10 via input port 12 from a liquid supply. The liquid initially enters a cold reservoir 14. A pump, not shown, controls the rate at which the unfiltered liquid flows into the filter 10. By maintaining a low flow velocity, the fluid flow throughout the filter will be laminar. Internal eddies or convection rolls will be generated in the filter if there are lateral temperature gradients. These convection rolls will destroy the filtration effect, and need to be minimized. The Reynolds numbers for the flow in the thermal gradient region should be much less than 1.

A thermoelectric cooler or Peltier cooler 16 pumps heat from reservoir 14 to the top of a lower reservoir 18. The cooler uniformly chills the liquid in the reservoir 14 so that it can act as a thermal sink in the subsequent filtering processes described hereinafter.

The chilled liquid in reservoir 14 flows through a conduit 20 into the cold plenum portion 22 of lower reservoir 18. In order to maintain the liquid in the cold plenum at a low temperature, a portion (preferably at least approximately one-half) of the liquid entering the cold plenum from conduit 20 immediately exits the cold plenum region 22 via exhaust outlet port 24. Due to the highly laminar flow of the liquid in the filter, the apparatus can be designed so that a predetermined portion of the liquid entering from conduit 20 exits via outlet port 24. A pump (not shown) is coupled to the outlet port 24 for controlling the quantity and flow rate of the liquid exiting the cold plenum region. The pump is selected to provide a uniform flow velocity to avoid creating turbulence in the cell, particularly turbulence in the thermal gradient region of the cell.

In an alternative embodiment, another cooler is coupled to the bottom surface of the cold plenum for maintaining the liquid in the cold plenum chilled without removing a portion of the liquid through an output port.

From the cold plenum 22 the remaining portion of the liquid flows upward through apertures 26 in a foil sheet 28 to a centrally disposed thermal gradient region 30 in lower reservoir 18. Preferably, the apertures are square shaped slots and at least 400 microns long on each side. Alternatively, the apertures can be of other configurations such as round or rectangular. The relatively large size of the slotted apertures in the sheet minimizes the possibility of clogging of the filter. The primary purpose of the sheet is to make the velocity profile in the thermal gradient region substantially uniform.

Almost all of the flow in the thermal gradient region 30 is in the horizontal direction as shown in the FIGURE and liquid exits through outlet port 32 as output brine. A pump (not shown) is coupled to the outlet port 32 for controlling the quantity and flow rate of the liquid exiting the thermal gradient region. The pump is selected to provide a uniform flow velocity to avoid creating turbulence in the thermal gradient region.

A small amount of the flow in the thermal gradient region 30 passes through apertures 34 in a second sheet 36 into a hot plenum-region 38 of lower reservoir 18. The construction of apertures 34 and sheet 36 is similar to the construction of slots 36 and sheet 28, however, the shape and dimension of the apertures may be the same or different in each sheet. The liquid exits the hot plenum region through outlet port 40 as output clean.

The sheets 28, 36 also provide a uniform temperature along the boundary regions between the cold plenum region and the thermal gradient region and between the hot plenum region and the thermal gradient region, respectively. The absence of a uniform temperature along the boundaries, in the horizontal direction as shown, will result in undesirable turbulence in the liquid in the thermal gradient region.

All of the thermally conducting areas of the filter are preferably made a good thermally conducting material which is generally non-reactive with most liquids encountered in semiconductor processes. Preferred materials include sapphire or stainless steel. The non-conducting surfaces are preferably made of a material which is inert with most liquids encountered in semiconductor processing. A preferred material is Teflon. This construction permits use of the filter with almost any liquid.

The thermophoretic velocity of a particle in a liquid may be expressed as:

$$V = \frac{3\eta H \delta T}{2\rho_1 T \delta x}$$

where
$\eta$ is the liquid viscosity;

$$H = \frac{k_1}{k_p},$$

where $k_1$ is the thermal conductivity of the liquid and $k_p$ is the thermal conductivity of the particle;

$$\frac{\delta T}{\delta x}$$

is the temperature gradient across the thermal gradient region;
$\rho_1$ is the density of the liquid, and
T is the absolute temperature of the particle.

The filter is "adjusted" so that the thermophoretic velocity, that is, the speed at which the thermal gradient urges the particles toward the cold plenum, must be greater than the average velocity of the flow passing through the upper foil sheet 36. The thermophoretic flow rate of the liquid is the product of the area of the sheet 36 multiplied by the thermophoretic velocity. In the apparatus shown in the FIGURE, the exiting flow velocity through outlet port 40 can be made arbitrarily slow so that the thermophoretic force need not be strong in order to achieve good separation of particles from the clean solution.

In a filter constructed as shown, a dense (greater than $10^{10}$ particles per cc) solution of 0.089 micron diameter polystyrene spheres was injected into cold reservoir 14 at a flow rate of approximately 10 milliliters per minute. Approximately half the liquid entering the cold plenum region 22 via conduit 20 exited directly via outlet port 24 for maintaining the liquid in region 22 chilled, i.e. for heat sinking. Approximately half the liquid entering from conduit 20 exited the thermal gradient region 30 via outlet port 32 as brine. The flow from outlet port 40 of clean liquid was maintained at approximately 0.03 milliliters per minute. The temperature difference across the thermal gradient region 30 was 18 degrees Centigrade. The liquid exiting outlet port 40 as clean solution appeared clear while the liquid exiting outlet port 24 and outlet port 32 appeared milky. Electrical power consumption by the thermocooler 16 was approximately 4 watts, of which at least 75 percent was waste heat.

In applications requiring even better filtering of a particle containing solution, a plurality of filters of the type shown in the FIGURE can be coupled in series where the clean liquid output of one thermophoretic filter is the input to the next stage thermophoretic filter. Due to the non-linear variations of the process, the filtering should improve at an exponential rate as additional filter stages are added in series. In order to increase the quantity of clean liquid, a plurality of filters can be coupled in a parallel relationship. It will be apparent to those skilled in the art that combinations of serially and parallel connected filters can be designed depending upon the filtering application.

While there has been described and illustrated a preferred embodiment of a thermophoretic filter for liquids, it will be apparent to those skilled in the art that modifications and variations are possible without deviating from the broad principle of the present invention which shall be limited solely by the scope of the claims appended hereto.

What is claimed is:

1. A method of thermophoretic filtering of particles from a liquid comprising the steps of:
   introducing a flow of chilled particle containing liquid into a reservoir so that the chilled liquid acts as a heat sink for the particles; and
   filtering the liquid within the reservoir through a thermal gradient region having a predetermined area at a flow rate less than the product of the thermophoretic velocity of the particles multiplied by the predetermined area.

2. A method of thermophoretic filtering of particles from a liquid as set forth in claim 1, wherein a portion of the chilled liquid introduced into the reservoir exits to maintain the liquid at a low temperature.

3. A method of thermophoretic filtering of particles from a liquid as set forth in claim 1, wherein the reservoir is separated into a cold plenum region, a thermal gradient region and a hot plenum region and a first aperture sheet separates the cold plenum region from the thermal gradient region and a second aperture sheet separates the thermal gradient region from the hot plenum region, whereby the liquid being filtered travels from the cold plenum region to the hot plenum region through the first and second aperture sheets.

4. A thermophoretic filter comprising:
   a reservoir into which a chilled particle containing liquid is introduced;
   means for maintaining the particle containing liquid at a low temperature so the liquid acts as a heat sink; and
   means for filtering the liquid within said reservoir through a thermal gradient region having a predetermined area at a flow rate less than the product of the thermophoretic velocity of the particles multiplied by the predetermined area.

5. A thermophoretic filter as set forth in claim 4 further comprising a cooling reservoir including cooling means for chilling the particle containing liquid prior to being introduced into said reservoir.

6. A thermophoretic filter as set forth claim 4, wherein said reservoir is separated into a cold plenum region, a thermal gradient region and a hot plenum region and further comprising a first aperture sheet disposed between said cold plenum region and said thermal gradient region and a second aperture sheet disposed between said thermal gradient region and said hot plenum region.

7. A thermophoretic filter as set forth in claim 6, further comprising a cooling reservoir including cooling means for chilling the particle containing liquid prior to being introduced into said reservoir.

8. A thermophoretic filter as set forth in claim 6, wherein the chilled liquid enters said cold plenum region and said means for maintaining the particle containing liquid at a low temperature comprises means for removing a portion of chilled particle containing liquid from said cold plenum region.

* * * * *